United States Patent [19]

Kurimura et al.

[11] Patent Number: 5,517,870
[45] Date of Patent: May 21, 1996

[54] INTRA-LIQUID PARTICLE CLASSIFICATION APPARATUS USING LIGHT SCATTERING

[75] Inventors: Masaaki Kurimura, Ibaraki; Masaaki Hanawa, Katsuta, both of Japan

[73] Assignee: Hitachi, Ltd., Tokyo, Japan

[21] Appl. No.: 168,509

[22] Filed: Dec. 22, 1993

[30] Foreign Application Priority Data

Dec. 25, 1992 [JP] Japan ..................................... 4-346657

[51] Int. Cl.$^6$ ................................................. G01N 15/00
[52] U.S. Cl. .................. 73/865.5; 73/864.12; 73/864.21
[58] Field of Search ............................. 73/865.5, 864.11, 73/864.12, 864.13, 864.15, 864.17, 864.21, 864.22, 864.24, 864.25, 864.34, 864.73, 864.81–.87, 864.91; 422/64, 100; 436/180

[56] References Cited

U.S. PATENT DOCUMENTS

| | | | |
|---|---|---|---|
| 3,583,230 | 6/1971 | Patterson | 73/864.85 |
| 3,600,953 | 8/1971 | Isreeli et al. | 73/864.81 |
| 3,669,542 | 6/1972 | Capellaro | 73/865.5 |
| 3,740,143 | 6/1973 | Groner et al. | 356/39 |
| 3,942,360 | 3/1976 | Wada | 73/865.5 |
| 4,003,708 | 1/1977 | Taguchi et al. | 422/81 |
| 4,240,429 | 12/1980 | Shackelford | 73/864.87 |
| 4,290,011 | 9/1981 | Berg et al. | 324/71.1 |
| 4,414,857 | 11/1983 | Brazhnikov et al. | 73/864.87 |
| 4,496,657 | 1/1985 | Coppersmith et al. | 435/287 |
| 4,564,803 | 1/1986 | Loren et al. | 324/71.1 |
| 4,598,596 | 7/1986 | Wiseman et al. | 73/864.25 |
| 4,781,459 | 11/1988 | Suzuki | 356/335 |
| 4,946,651 | 8/1990 | Liston et al. | 73/864.91 |
| 5,079,959 | 1/1992 | Miyake et al. | 73/864.85 |
| 5,088,816 | 2/1992 | Tomioka et al. | 356/39 |
| 5,215,519 | 6/1993 | Shettigar | 604/6 |
| 5,245,318 | 9/1993 | Tohge et al. | 73/199 |

FOREIGN PATENT DOCUMENTS

| | | | |
|---|---|---|---|
| 474187 | 3/1992 | European Pat. Off. | 73/865.5 |
| 2547843 | 4/1977 | Germany | 73/864.22 |
| 38138 | 2/1988 | Japan | 73/865.5 |
| 4025746 | 1/1992 | Japan | 73/865.5 |
| 308354 | 7/1971 | U.S.S.R. | 73/865.5 |

Primary Examiner—Hezron E. Williams
Assistant Examiner—Daniel S. Larkin
Attorney, Agent, or Firm—Antonelli, Terry, Stout & Kraus

[57] ABSTRACT

A liquid sample is sucked from a staining vessel by a first sampling nozzle and the liquid sample is discharged into a flow cell unit, the liquid sample being supplied to the staining vessel by a second sampling nozzle so as to be stained in the staining vessel in advance. When the liquid sample is being discharged through the first sampling nozzle, a sheath liquid is supplied to a flow cell so that the sheath liquid flows with the liquid sample included therein. In this condition, passage of particles in the flow cell is detected by an optical system for detection at a still frame image pick-up position, and after a predetermined delay time based on the detection, strobe light is radiated so as to pick up a still frame image due to the scattered light to thereby perform classification and counting of the particles. Foreign matter in the liquid sample discharged from the sampling nozzle is caught by a filter and exhausted by the sheath liquid which overflows to the upper portion of the filter after completion of discharge of the liquid sample from the sampling nozzle. Bubbles in the flow cell are removed through an air vent and bubbles in the sheath liquid are removed after once reserved in an air vent chamber. Thus, foreign matter/bubbles in the liquid sample/sheath liquid can be prevented from entering the flow cell unit to make it possible to perform testing with high accuracy without lowering testing efficiency.

4 Claims, 5 Drawing Sheets

INTRA-LIQUID PARTICLE CLASSIFICATION APPARATUS USING LIGHT SCATTERING

BACKGROUND OF THE INVENTION

The present invention relates to an intra-liquid particle classification apparatus using light scattering, in which classification and counting of particles are carried out on the basis of an image obtained by light scattering of particles in a liquid sample such as blood, urine, etc.

Such a particle classification apparatus is an apparatus for resting particles in a liquid sample such as blood or urine in a hospital, a testing center, etc. That is, a liquid sample is made to be contained by a sheath liquid serving as an outer layer thereof to form a stationary flow having a flat section, that is, a sheath flow in a flow cell. The liquid sample in the flow cell is irradiated with strobe light of short light-emitting time, then the scattered light is picked up by an image pickup unit to thereby obtain a still frame image. The still frame image is processed in an image processing to thereby classify and count particles in the liquid sample. In most cases, particles suspended in the liquid sample are stained in a stain liquid so as to facilitate discrimination using light scattering.

An example of conventional particle classification apparatuses is disclosed in U.S. Pat. No. 5,088,816. In this particle classification apparatus, a liquid sample is sucked by a determination device so as to be temporarily reserved in a flowing vessel. An electromagnetic valve provided in the flowing vessel is switched so that the liquid sample is led into a reaction vessel by a suction pump. The electromagnetic valve is further switched so that the liquid sample having been reacted is sucked from the reaction vessel by the determination device and introduced into a flow cell. In this occasion, the liquid sample in the flow cell flows from the upper portion toward the lower portion. The liquid sample flowing in the flow cell is periodically irradiated with strobe light, and particles in the liquid sample is image-picked up as a still frame image by an image pickup unit using this strobe light. Then, classification and counting (hereinafter referred to as "test" occasionally) of the particles in the liquid sample are carried out based on the picked-up still frame image. Further, a filter for removing foreign matter such as dust is provided in an upstream portion of the flowing vessel, so that mixed foreign matter is removed by the filter.

SUMMARY OF THE INVENTION

In the conventional technique described in U.S. Pat. No. 5,088,816, the movement of the liquid sample from the sample vessel to the flow cell of the testing portion is carried out through the flowing vessel, so that the length of the flowing vessel is avoidably increased. Further, the distance between the flow cell and the filter for removing foreign matter mixed into the liquid sample is so long that there is a fear that foreign matter may be mixed from the flowing vessel disposed therebetween, or from the reaction vessel, a sheath liquid vessel, etc. on the way.

It is indeed possible to remove such foreign matter if a filter is provided at another place near the flow cell in the flowing vessel since, in the particle classification apparatus of the present invention, the direction of flow to lead the liquid sample into the flow cell is always fixed in one direction. However, there is a possibility that the filter is choked with foreign matter when a large quantity of foreign matter is deposited on the filter. As a consequence, it is necessary to exchange the filter like that, and testing must be stopped during the exchange of the filter to thereby lower the efficiency of classification and counting of particles.

Further, because the liquid sample is made to pass through the long flowing vessel between the sample vessel and the flow cell of the testing portion, air dissolved in the liquid sample easily changes into bubbles when the temperature of the liquid sample rises and these bubbles enter into the flow cell. When -the bubbles entering the flow cell are image-picked up together with particles, the bubbles may erroneously be detected as particles in the image processing of the picked-up still frame image, so that testing cannot be carried out with a high accuracy.

On the other hand, the applicants of the present invention invented an apparatus like the thus constituted particle classification apparatus which detects the passage of particles and obtains a still frame image synchronously with the detection of the particles without illuminating a strobe light source periodically, in order to pick up particles in a liquid sample with a high efficiency. With respect to this invention, the applicants have filed patent applications on Feb. 16, 1993 as U.S. patent application Ser. No. 08/018,371 corresponding to Japanese Patent Application No. 4-300802. In such an apparatus, an optical system for detecting particles is provided on the upstream side of the passageway of the liquid sample, that is, the passageway of the particles, independently of an optical system for picking up a still frame image, so that a particle detector detects the passage of particles when the particles cross the light (laser light) which is always emitted from a light source for detecting particles. When a predetermined delay time has passed after this detection, a light-emission pulse is supplied to the strobe light source so as to make the strobe light source emit strobe light to thereby obtain a still frame image of the particles. As a result, since strobe light is not emitted periodically, a vain still frame image which has failed to image-pick up particles is not formed, and particles which should be picked up are not overlooked, so that it is possible to improve the efficiency of testing.

In such a particle classification apparatus having an optical system for detecting particles, however, even in the case where foreign matter such as dust or bubbles pass through the flow cell, these foreign matter or bubbles are judged and detected as particles by mistake by the optical system for detecting particles, so that a vain still frame image is picked up. With picking up such a vain still frame image, the accuracy or efficiency on the classification or counting of particles is lowered. Particularly in a hospital or a testing center, liquid samples are often left as they are after blood gathering or urine gathering, so that it is inevitable that foreign matter such as dust is mixed into such a liquid sample or bubbles are produced therein, and hence it is inevitable to pick up a vain still frame image as mentioned above. In view of the above problems, it is an object of the present invention to provide an intra-liquid particle classification apparatus using light scattering, in which foreign matter or bubbles in a liquid sample or a sheath liquid can be prevented from entering a flow cell unit so that highly accurate testing can be performed without lowering the efficiency of the testing.

To achieve the foregoing object, according to an aspect of the present invention, in an intra-liquid particle classification apparatus using light scattering including a flow cell unit for forming a flat flow from a liquid sample and a sheath liquid, a sheath liquid supply unit for supplying the sheath liquid to the flow cell unit, in which the liquid sample in the flow cell unit is irradiated with light so that classification and counting of particles in the liquid sample are carried out on the basis of an image formed by the light scattered by the liquid sample, the apparatus further includes: a sampling nozzle for sucking the liquid sample and discharging the liquid sample into the flow cell unit; a moving mechanism for moving the sampling nozzle to the flow cell unit; a foreign matter catching unit disposed at an inlet of the flow cell unit so as to catch foreign matter in the liquid sample; a foreign matter removing unit for flowing back the sheath liquid from the flow cell unit so as to remove the foreign matter caught in the foreign matter catching unit; and a bubble removing unit for removing bubbles in the flow cell unit and in the sheath liquid.

In the present invention configured as described above, the sampling nozzle which has sucked a liquid sample is moved to the flow cell unit by the moving unit, so that a long flowing vessel for feeding the liquid sample as used in the prior art disclosed in U.S. Pat. No. 5,088,816 is not required. Accordingly, it is possible to reduce the probability that foreign matter is mixed into the liquid sample, and it is also possible to lower the possibility that bubbles are produced in the liquid sample by air dissolved in the sample in response to a change of temperature.

Further, if foreign matter is mixed into the liquid sample, the foreign matter is caught by the foreign matter catching unit disposed at the inlet of the flow cell unit when the liquid sample is discharged from the sampling nozzle to the flow cell unit. Then, the foreign matter caught thus is removed by the foreign matter removing unit. At this time, the removal of foreign matter is performed by flowing back the sheath liquid from the flow cell unit. Accordingly, it is not necessary to stop the testing wastefully to wash foreign matter or exchange the filter, so that foreign matter in the liquid sample can be removed efficiently and thoroughly.

Further, bubbles produced in the flow cell unit and in the sheath liquid due to temperature rising or the like are removed by the bubble removing unit.

Preferably, the apparatus mentioned above further includes a washing bath for washing the sampling nozzle, and a washing liquid supply unit for supplying a washing liquid to the washing bath, wherein the sampling nozzle is moved to the washing bath by the moving mechanism.

That is, the sample nozzle is moved also to the washing bath by the moving mechanism, and the sampling nozzle is washed in this washing bath with the washing liquid supplied from the washing liquid supply unit. Further, because the quantity of the liquid sample required for testing may be as small as the volume of the sampling nozzle, the apparatus may be applied to a blood test and a urine test for infants or the like from whom a large quantity of sample cannot be taken out, and the quantity of the washing liquid required at the time of washing of the sampling nozzle may be also small.

Further, to attain the foregoing object, according to another aspect of the present invention, in an intra-liquid particle classification apparatus using light scattering including a staining vessel for staining particles in a liquid sample with a stain liquid, a flow cell unit for forming a flat flow by the liquid sample stained in the staining vessel and a sheath liquid, and a sheath liquid supply unit for supplying the sheath liquid to the flow cell unit, in which the liquid sample in the flow cell unit is irradiated with light so that classification and counting of particles in the liquid sample are carried out on the basis of an image formed by the scattered light by the liquid sample, the apparatus further includes: a first sampling nozzle for sucking the liquid sample stained in the staining vessel and for discharging the liquid sample into the flow cell unit; a first moving mechanism for moving the first sampling nozzle between the staining vessel and the flow cell unit; a foreign matter catching unit disposed at an inlet of the flow cell unit so as to catch foreign matter in the liquid sample; a foreign matter removing unit for flowing back the sheath liquid from the flow cell unit so as to remove the foreign matter caught in the foreign matter catching unit; and a bubble removing unit for removing bubbles in the flow cell unit and in the sheath liquid.

Thus, in the case where particles in the liquid sample is to be stained in the staining vessel, the sampling nozzle is moved also to the staining vessel by the moving mechanism.

Preferably, in the above-mentioned configuration, the apparatus further includes a first washing bath for washing the first sampling nozzle, and a first washing liquid supply unit for supplying a washing liquid to the first washing bath, wherein the first moving mechanism moves the first sampling nozzle also to the first washing bath.

Preferably, the apparatus further includes a second sampling nozzle for supplying the liquid sample into the staining vessel, and a second moving mechanism for moving the second sampling nozzle to the staining vessel.

Preferably, the apparatus further includes a second washing bath for washing the second sampling nozzle, and a second washing liquid supply unit for supplying a washing liquid to the second washing bath, wherein the second moving mechanism moves the second sampling nozzle also to the second washing bath.

In the above case, the liquid sample is supplied to the staining vessel by the second sampling nozzle. By providing the second sampling nozzle in such a manner, distribution of the liquid sample to the staining vessel and discharge of the stained liquid sample to the flow cell unit can be carried out simultaneously to thereby further improve the efficiency of testing. Further, the second sampling nozzle is washed in the second washing bath.

In the intra-liquid particle classification apparatus configured thus, preferably, the bubble removing unit includes an air vent port opened in an upper portion of the flow cell unit and for removing bubbles produced in the flow cell unit.

Thus, bubbles produced in the flow cell unit are removed from the air vent port opened in the upper portion of the flow cell.

Preferably, the bubble removing unit includes an air vent chamber communicated with the sheath liquid supply unit so as to reserve bubbles produced in the sheath liquid, and an air outlet for discharging bubbles reserved in the air vent chamber.

Thus, bubbles produced in the sheath liquid are reserved in the air vent chamber communicated with the sheath liquid supply unit, and the bubbles reserved in the air vent chamber are discharged from the air outlet.

Preferably, the flow cell unit includes a flow cell for making the liquid sample included in the sheath liquid to thereby form a flat flow, a flow cell nozzle having an upper portion brought into close contact with a forward end portion of the sampling nozzle so as to supply the flow cell with the liquid sample supplied from the sampling nozzle, a sealing unit for sealing a close contact portion between the sampling nozzle and the flow cell nozzle, and a sheath liquid inlet for supplying the flow cell with the sheath liquid supplied from the sheath liquid supply unit.

In such a flow cell unit as mentioned above, a forward end portion of the sampling nozzle comes into close contact with an upper portion of the flow cell nozzle to thereby form a liquid sample discharge passage. The close contact portion between the sampling nozzle and the flow cell nozzle is sealed by the sealing unit to prevent the liquid sample from leaking out from this portion. Further, a sheath liquid is supplied from the outside of the discharge passage through the sheath liquid inlet, so that the liquid sample is included in the sheath liquid in the flow cell to thereby form a flat and stationary flow. Then, the flow cell is irradiated with light so that classification and counting of particles in the liquid sample are carried out on the basis of an image formed by the light scattered by the liquid sample.

Preferably, in the above-mentioned case, the foreign matter catching unit is a filter provided in an inlet of the flow cell nozzle.

Further preferably, the foreign matter removing unit includes an exhaust port provided on the upstream side of the foreign matter catching unit.

Accordingly, foreign matter in the liquid sample discharged from the sampling nozzle is caught by the filter provided at the inlet of the flow cell nozzle. Then, the sheath liquid is made to flow back from the sampling nozzle so as to overflow to the upstream side of the filter so that the foreign matter caught by the filter is removed from the exhaust port with the overflowing sheath liquid when discharge of the liquid sample from the sampling nozzle is completed and the sampling nozzle is moved away from the flow cell nozzle by the moving mechanism.

BRIEF DESCRIPTION OF THE DRAWINGS

FIG. 2 is a schematic view when FIG. 1 is viewed from above, for explaining the movement and operation of a sampling nozzle;

DESCRIPTION OF THE PREFERRED EMBODIMENT

Referring to FIGS. 1 through 4, an embodiment of the intraliquid particle classification apparatus using light scattering according to the present invention will be described below.

Figure 1:
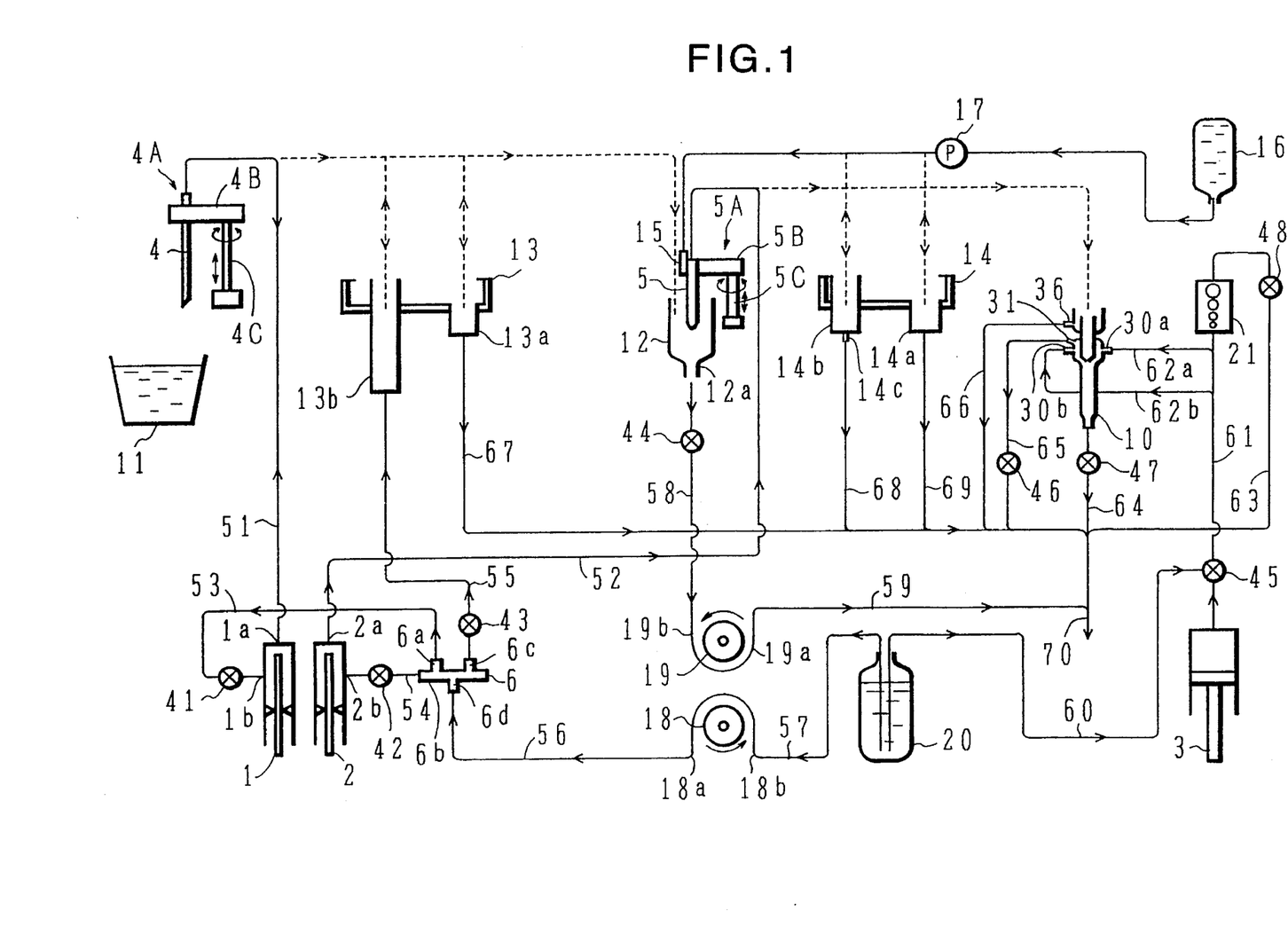
FIG. 1 is a schematic diagram of a passage piping arrangement showing an embodiment of an intra-liquid particle classification apparatus using light scattering according to the present invention.

Referring now to FIG. 1, the structure of the particle classification apparatus of this embodiment will be described. In FIG. 1, syringe pumps 1, 2 and 3 are driven by not shown driving motors to suck/discharge a liquid sample. A suction/discharge port 1a of the syringe pump 1 is connected to a sampling nozzle 4 through a tube 51. A suction/discharge port 2a of the syringe pump 2 is connected to a sampling nozzle 5 through a tube 52.

One end 6a of a branch pipe 6 is connected to a side port 1b of the syringe pump 1 through a tube 53 and an electromagnetic valve 41. Another end 6b of the branch pipe 6 is connected to a side port 2b of the syringe pump 2 through a tube 54 and an electromagnetic valve 42. A further end 6c of the branch pipe 6 is connected to a washing pipe 13b through an electromagnetic valve 43 and a tube 55. A further end 6d of the branch pipe 6 is connected to a discharge side 18a of a peristyle pump 18 through a tube 56.

The sampling nozzle 4 can be moved among a sample cup 11, a drain 13a of a washing bath 13, the washing pipe 13b of the washing bath 13 and a staining vessel 12 by a lift 4A which is a moving mechanism. On the other hand, the sampling nozzle 5 can be moved among the staining vessel 12, a drain 14a of a washing bath 14, a washing pipe 14b of the washing bath 14 and a flow cell unit 10, by a lift 5A which is a moving mechanism. For the sake of simplification, the lifts 4A and 5A are shown typically in FIG. 1 while the moving paths of the sampling nozzles 4 and 5 are shown by the broken line in the drawing.

Figure 2:
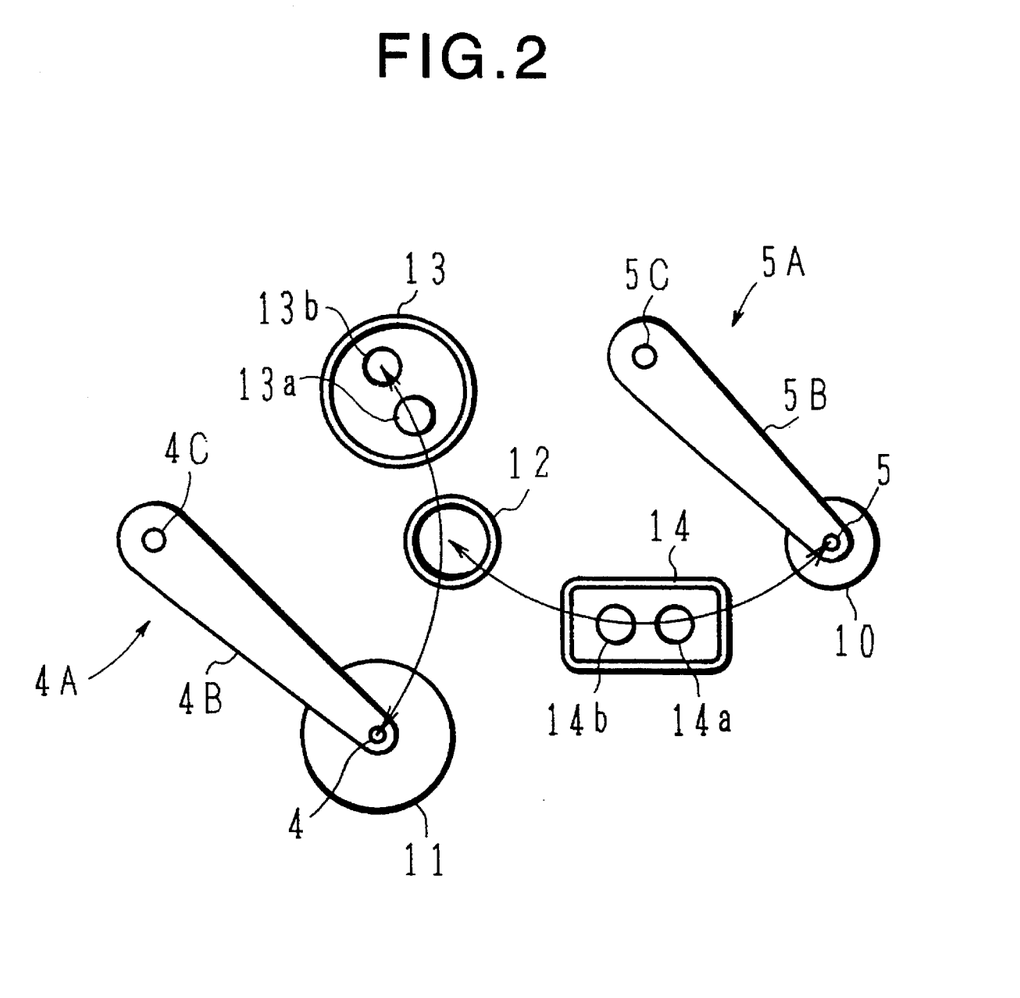

The operation of movement of the sampling nozzles 4 and 5 will be described with reference to FIG. 2. The lift 4A has a rotary shaft 4C and an arm 4B. The arm 4B moves up and down and rotates as the rotary shaft 4C moves up and down and rotates. In the same manner, the lift 5A has a rotary shaft 5C and an arm 5B. The arm 5B moves up and down and rotates as the rotary shaft 5C moves up and down and rotates. In FIG. 2, the sampling nozzle 4 moves on a circumference with the rotary shaft 4C of the lift 4A as its center and with the length of the arm 4B as its radius. Then, the sampling nozzle 4 moves up and down at the respective places of the sample cup 11, the staining vessel 12, the drain 13a of the washing bath 13, and the washing pipe 13b of the washing bath 13 all of which are provided on this circumference. On the other hand, the sampling nozzle 5 moves on a circumference with the rotary shaft 5C of the lift 5A as its center and with the length of the arm 5B as its radius. Then, the sampling nozzle 5 moves up and down at the respective places of the staining vessel 12, the drain 14a of the washing bath 14, the washing pipe 14b of the washing bath 14, and the flow cell unit 10 all of which are provided on this circumference. The operation of movement of such sampling nozzles is described in detail in U.S. Pat. No. 5,079,959 and in Japanese Patent Application Serial No. 2-296131.

Referring to FIG. 1 again, the distal end of a discharge nozzle 15 is fixed toward the inside of the staining vessel 12 so that a stain liquid in a stain liquid bottle 16 is fed out to the staining vessel 12 through the discharge nozzle 15 by a feed pump 17.

The peristyle pump 18 has a suction side 18b connected, through a tube 57, to a washing liquid bottle 20 for supplying a washing liquid which serves also as a sheath liquid, so that the peristyle pump 18 is used for feeding the washing liquid in the washing liquid bottle 20 to the branch pipe 6. On the other hand, a peristyle pump 19 is used for discharging a liquid sample from the staining vessel 12. A suction side 19b of the peristyle pump 19 is connected to an exhaust port 12a at the lower portion of the staining vessel 12 through a tube 58 and an electromagnetic valve 44. Further, a discharge side 19a of the peristyle pump 19 is connected to an exhaust tube 59.

A three-way electromagnetic valve 45 is connected to the syringe pump 3. A side of the three way electromagnetic valve 45 is connected to the washing liquid bottle 20 through a tube 60, while another side of the valve 45 is connected to a lower portion of an air vent chamber 21 through a tube 61 and further connected to two sheath liquid inlets 30*a* and 30*b*, which will be described later, of the flow cell unit 10 through respective tubes 62*a* and 62*b* branching from the tube 61. A washing liquid which serves also as a sheath liquid is stored in advance in the syringe pump 3 from a washing liquid bottle 20. The air vent chamber 21 serves to reserve bubbles in the case where air dissolved in the sheath liquid (washing liquid) sent out by the syringe pump 3 changes into bubbles due to temperature changes or the like. At an upper portion of the air vent chamber 21, an exhaust tube 63 is connected thereto through an electromagnetic valve 48.

An exhaust tube 64 is connected to a lower portion of the flow cell unit 10 through an electromagnetic valve 47. An electromagnetic valve 46 and an exhaust tube 65 are connected to an air vent port 31, which will be described later, provided at the same height as that of the inlets 30*a* and 30*b* of the flow cell unit 10. An exhaust tube 66 is connected to a waste liquid nozzle 36, which will be described later, serving as an exhaust passage provided at an upper portion of the flow cell unit 10. An exhaust tube 67 is connected to a lower portion of the drain 13*a* of the washing bath 13. Similarly, exhaust tubes 68 and 69 are connected to lower portions of the drain 14*a* and washing pipe 14*b* of the washing bath 14, respectively. The aforementioned exhaust tubes 59, 63, 64, 65, 66, 67, 68 and 69 are collectively connected to a waste liquid port 70. In the above description, each of the electromagnetic valves 41, 42, 43, 44, 46, 47 and 48 is a two-way electromagnetic valve which is normally closed but opened by current conduction thereto.

Figure 3:
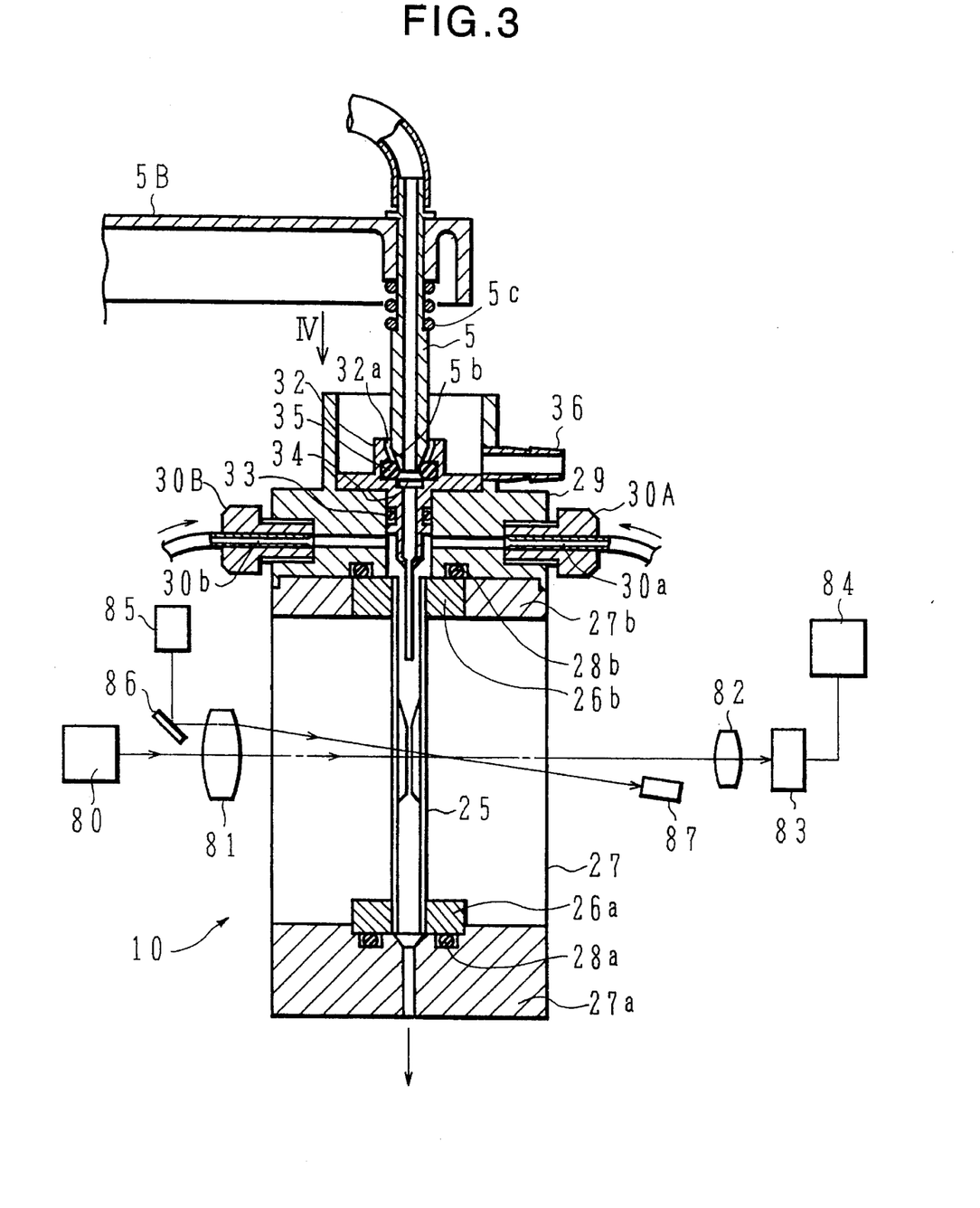
FIG. 3 is a schematic sectional view of a flow cell unit in FIG. 1, showing the condition in which the sampling nozzle is in close contact with the flow cell unit.
Figure 4:
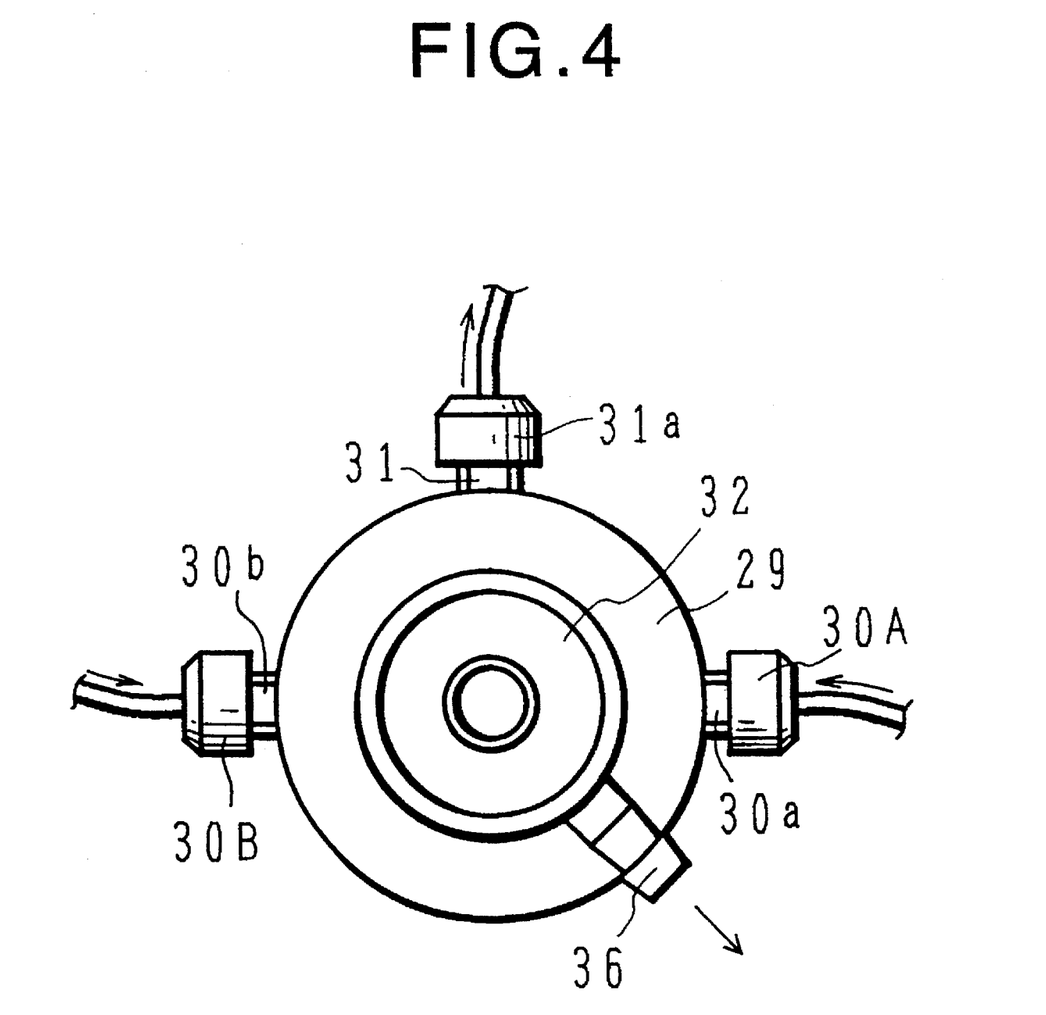
FIG. 4 is a schematic plan view of the flow cell unit of FIG. 2 when viewed from the IV direction, showing the condition in which the sampling nozzle is not in close contact with the flow cell unit.

Referring next to FIGS. 3 and 4, the structure of the flow cell unit 10 will be described in detail. FIG. 3 is a view showing the condition in which the sampling nozzle 5 is brought in close contact with the flow cell unit 10.

This embodiment employs a method of discharging a liquid sample while bringing the sampling nozzle into close contact with the flow cell unit by moving the sampling nozzle directly to the flow cell unit. Accordingly, a flow cell in the flow cell unit is of a vertical type so that the liquid sample is made to flow from its upper side to its lower side. As shown in FIG. 3, in the flow cell unit 10, circular flanges 26*a* and 26*b* of the same diameter are parallelly fixed to upper and lower portions of a flow cell 25 which is made of transparent glass. The flange 26*a* is disposed vertically in a center portion of a flow cell supporting portion 27*a* at a lower portion of a flow cell stand 27 and is sealed by an O-ring 28*a*. The flange 26*b* is disposed vertically so as to pierce a center portion of a flow cell supporting portion 27*b* at an upper portion of the flow cell stand 27 and is sealed by an O-ring 28*b*. As shown in FIG. 4, two sheath liquid inlets 30*a* and 30*b* sealed by joints 30A and 30B respectively are disposed in opposite relation therebetween in a flow cell holder 29 fixed to an upper portion of the flow cell stand 27. These sheath liquid inlets 30*a* and 30*b* are connected to the syringe pump 3 through the respective tubes 62*a* and 62*b* as described above. The sheath liquid inlets 30*a* and 30*b* constitutes a sheath liquid supply means together with the tubes 62*a* and 62*b*.

On the other hand, an air vent port 31 having the same shape as those of the sheath liquid inlets 30*a* and 30*b* and disposed at the same height as the height of the two inlets is provided at a position in the midway between the sheath liquid introduction ports 30*a* and 30*b*, that is, at a position away by 90 degrees from each of the sheath liquid inlets 30*a* and 30*b* and is sealed by a joint 31*a*. As described above, the exhaust tube 65 and the electromagnetic valve 46 are connected to the air vent port 31. The air vent port 31 serves to remove bubbles accumulated in an upper portion of the inside of the flow cell 25. Although this embodiment shows the case where one air vent port is provided, it is a matter of course that a plurality of air vent ports may be provided. The aforementioned air vent port 31, the tube 65 and the electromagnetic valve 46 cooperate with the air vent chamber 21, the electromagnetic valve 48 and the tube 63 to constitute a bubble removing means (see FIG. 1).

Returning to FIG. 3, a flow cell nozzle 32 is inserted in a center portion of the flow cell holder 29 and fixed thereto. The flow cell nozzle 32 is sealed with respect to the flow cell holder 29 by an O-ring 33. A filter 34 which is a foreign matter catching means is mounted on an upper opening portion 32*a* of the inlet of the flow cell nozzle 32. An O-ring 35 is disposed in an upper portion of the filter 34. As shown in the drawing, the upper opening portion 32*a* of the flow cell nozzle 32 has a shape which is allowed to come into contact with a taper portion 5*b* at a forward end of the sampling nozzle 5. On the other hand, the sampling nozzle 5 is pressed against the flow cell nozzle 32 with a predetermined amount of pressure through the O-ring 35 by a push spring 5*c* so as to be in close contact with the flow cell nozzle 32. The sampling nozzle 5 and the flow cell nozzle 32 are sealed with respect to each other by the actions of the push spring 5*c* and the O-ring 35 so that a passage for discharging the liquid sample is formed. The filter 34 is a mesh filter which serves to remove foreign matter such as dust in the sample.

The respective center lines of the sampling nozzle 5, the flow cell nozzle 32 and the flow cell 25 are aligned so that the sheath liquid from the two sheath liquid inlets 30*a* and 30*b* is supplied from the outside of the passage for discharging the liquid sample constituted by the sampling nozzle 5 and the flow cell nozzle 32 and includes the liquid sample in the inside of the flow cell 25 to form a flat and stationary flow. In this embodiment, the sheath liquid is made to serve also as a washing liquid for the sampling nozzle.

Further, a waste liquid nozzle 36 which is an exhaust passage is provided at an upper portion of the flow cell holder 29 and is connected to the aforementioned exhaust tube 66. The opening position of the exhaust nozzle 36 is on the upstream side of the filter 34. Accordingly, as will be described later, when the electromagnetic valve 47 is closed to make the sheath liquid overflow from the upper opening portion 32*a* of the flow cell nozzle 32, foreign matter caught by the filter 34 is carried by the sheath liquid so as to be discharged out of the exhaust nozzle 36. The exhaust nozzle 36 and the tube 66 cooperate with the upper opening portion 32*a* of the flow cell nozzle 32 and the electromagnetic valve 47 to constitute a foreign matter removing means. Further, the flow cell unit 10 is provided with an optical system for picking up an image of particles in the liquid sample. The optical system is constituted by a pulse light source 80, a condenser lens 81, an objective lens 82, a CCD camera 83 and an image analyzer 84. The flow cell unit 10 is further provided with another optical system for detecting particles in the liquid sample. The other optical system is constituted by a laser light source 85, a total reflection mirror 86 and a detector 87. The optical systems for picking up an image and detecting particles in the liquid sample are described in detail in U.S. patent application Ser. No. 08/018,371 corresponding to Japanese Patent Application No. 4-300802 which have been filed by the applicants of the present invention.

In the following, the operation of the intra-liquid particle classification apparatus using light scattering as configured above will be described.

First, when the sampling nozzle 4 is moved down by the lift 4A so as to rush into the liquid sample in the sample cup 11, a predetermined quantity of the liquid sample is sucked by the syringe pump 1. Then, the sampling nozzle 4 moves to the staining vessel 12 so that the liquid sample is discharged into the staining vessel 12. Although the stain liquid in the stain liquid bottle 16 is sent out by the feed pump 17 and discharged into the staining vessel 12 through the discharge nozzle 15, the liquid sample and the stain liquid can be stirred by the discharge pressure of the liquid sample when the liquid sample is discharged from the sampling nozzle 4 if the stain liquid is discharged into the staining vessel 12 in advance.

Upon completion of the discharge, the sampling nozzle 4 moves to the drain 13a of the washing bath 13 and at the same time the electromagnetic valve 41 is opened. As a result, the washing liquid in the washing liquid bottle 20 is sent out to the sampling nozzle 4 via the tube 56, the branch pipe 6 and the tube 53 by the pumping action of the peristyle pump 18. The washing liquid then enters the syringe pump 1 at the side port 1b and is discharged from the suction/discharge port 1a and sent to the sampling nozzle 4 via the tube 51 whereby the inner surface of the sampling nozzle 4 is washed by the washing liquid. The washing liquid thus discharged is drawn off through the tube 67. After washing, the electromagnetic valve 41 is closed.

Then, the sampling nozzle 4 is moved down to the washing pipe 13b of the washing bath 13 and at the same time the electromagnetic valve 43 is opened. As a result, the washing liquid is supplied to the lower portion of the washing pipe 13b via the branch pipe 6 and the tube 55 and overflows from the upper portion of the washing pipe 13b so that the outer surface of the sampling nozzle 4 is washed. The washing liquid thus overflown is discharged from the drain 13a of the washing bath 13 through the tube 67. After washing, the electromagnetic valve 43 is closed.

On the other hand, the liquid sample in the staining vessel 12 is left as it is for a predetermined time so that particles in the liquid sample are stained by the stain liquid. After completion of staining, the sampling nozzle 5 is moved down into the staining vessel 12 by the lift 5A so that a predetermined quantity of the liquid sample is sucked by the syringe pump 2. When the sampling nozzle 5 moves down to the flow cell unit 10 so as to come into close contact with the flow cell nozzle 32, the sampling nozzle 5 and the flow cell nozzle 32 are sealed by the push spring 5c and the O-ring 35.

Then, the syringe pump 2 is driven in the discharge direction so that the liquid sample in the sampling nozzle 5 flows into the flow cell 25 via the filter 34 and the flow cell nozzle 32. At this time, foreign matter such as dust is caught by the filter 34. At the same time, the three-way electromagnetic valve 45 is switched to the tube 61 side to drive the syringe pump 3 in the discharge direction so that the sheath liquid acting also as washing liquid stored in the syringe pump 3 flows in from the two sheath liquid inlets 30a and 30b of the flow cell holder 29. As a result, in a narrow portion of the flow cell 25, the liquid sample is included by the sheath liquid to form a stationary flow having a flat section, that is, a sheath flow, so that the sheath liquid passes through the flow cell 25 at a constant speed. Further, the electromagnetic valve 47 is opened, so that the liquid sample and the sheath liquid which have passed through the flow cell 25 are discharged through the exhaust tube 64. In this occasion, that is, at the time of testing, the electromagnetic valves 46 and 48 are closed.

The flow cell 25 is irradiated with laser light for detecting particles from the laser light source 85 through the total reflection mirror 86 and the condenser lens 81. If particles come across the laser light in the liquid sample, the detector 87 detects the passage of particles. If the passage of particles is detected by the detector 87, strobe light of short emitting time is generated from the pulse light source 80 after a predetermined delay time. This strobe light is transmitted through the condenser lens 81 to a still frame image picking up position in the flow cell 25, and the light scattered from the flow cell 25 is collected by the objective lens 82 so that the still frame image is picked up by the CCD camera 83. On the basis of the still frame image picked up by the CCD camera 83, classification and counting of particles are carried out by the image analyzer 84 (see FIG. 3). In the flow cell 25, the irradiation position with the laser light for detecting particles is upwardly separated by a predetermined distance from the still frame image picking up position, and the aforementioned delay time is set to the time taken for the liquid sample to flow over this distance. By providing an optical system for detecting particles in such a manner, there occurs no case where a useless still frame image missing particles is picked up.

Figure 5:
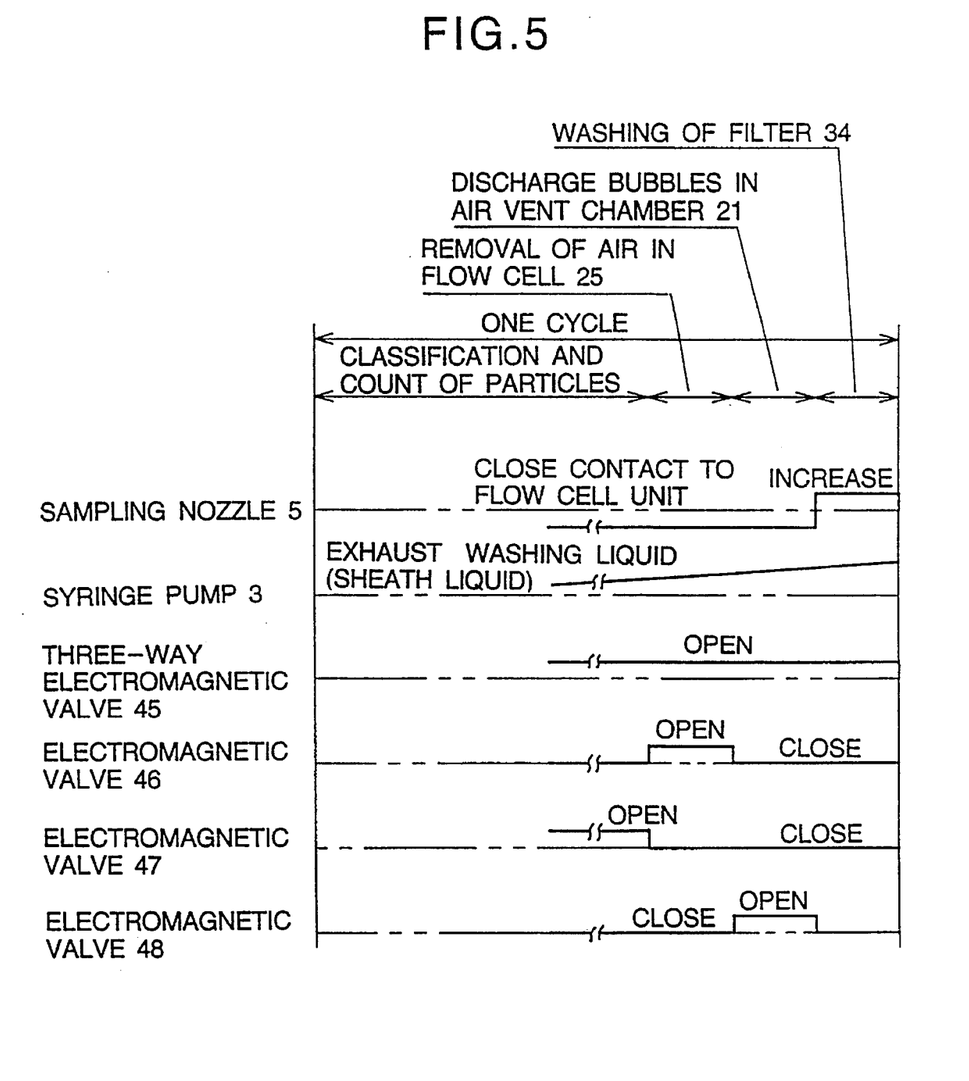
FIG. 5 is a timing chart showing the operation of the sampling nozzle, a syringe pump, a three-way electromagnetic valve and other electromagnetic valves after completion of classification and counting of particles in one sample.

Upon completion of classification and count of particles in one sample and upon completion of discharge of the liquid sample, the electromagnetic valves 47 and 48 are closed and the electromagnetic valve 46 is opened as shown in the time chart of FIG. 5 while the sampling nozzle 5 is kept continuously in close contact with the flow cell nozzle 32. The syringe pump 3 is continuously driven so that the sheath liquid in the flow cell 25 is compressed. As a result, bubbles produced in the flow cell 25 are discharged out of the air vent port 31. Then, the electromagnetic valves 46 and 47 are closed and the electromagnetic valve 48 is opened. The syringe pump 3 is continuously driven so that the sheath liquid in the air vent chamber 21 is compressed. As a result, bubbles stored in the air vent chamber 21 are discharged through the exhaust tube 63. The aforementioned order with respect to the removal of bubbles in the flow cell 25 and the removal of bubbles in the air vent chamber 21 may be exchanged.

In the test thus carried out in such a manner as described above, foreign matter and bubbles may be mistaken for target particles by the aforementioned detecting optical system if they are fed and mixed into the flow cell 25. In this embodiment, however, foreign matter in the sample is caught by the filter 34 so that such foreign matter is prevented from being mixed in the flow cell 25, and bubbles are removed in the aforementioned manner so that such bubbles are also prevented from being mixed in the flow cell 25.

Then, the sampling nozzle 5 moves up far from the flow cell nozzle 32 and at the same time the electromagnetic valves 46, 47 and 48 are closed as shown in FIG. 5. The syringe pump 3 is continuously driven so that the sheath liquid is continuously supplied through the sheath liquid inlets 30a and 30b. The sheath liquid flows backward from the lower portion and overflows from the upper opening portion 32a of the flow cell nozzle 32. The sheath liquid thus overflown is discharged from the waste liquid nozzle 36 through the exhaust tube 66. Foreign matter caught by the filter 34 is carried by the overflowing sheath liquid and drawn off. The seal portion of the O-ring 35 is washed with the overflowing sheath liquid so that foreign matter in this portion is also drawn off. Because the area of the filter 34 can be reduced, the carry-over and dead volume from the preceding sample can be reduced.

The sampling nozzle 5 separated up from the flow cell nozzle 32 moves to the drain 14a of the washing bath 14 and at the same time the electromagnetic valve 42 is opened. As a result, in the same manner as the washing of the inner surface of the sampling nozzle 4, the washing liquid in the washing liquid bottle 20 is sent out via the tube 56, the branch pipe 6 and the tube 54 by the peristyle pump 18, then enters the syringe pump 2 at the side port 2b and is discharged from the suction/discharge port 2a and sent to the smapling nozzle 5 via the tube 52 so that the inner surface of the sampling nozzle 5 is washed by the washing liquid. The washing liquid thus discharged is drawn off via the tube 69. After washing, the electromagnetic valve 42 is closed.

Then, the sampling nozzle 5 moves to the washing pipe 14b of the washing bath 14 and at the same time the electromagnetic valve 42 is opened. As a result, like the above description, the washing liquid is fed to the sampling nozzle 5 via the tube 52 from the suction/discharge port 2a. The quantity of waste liquid in the waste liquid port 14c at the bottom of the washing pipe 14b is selected to be smaller than the quantity of discharge in the sampling nozzle 5, so that the washing liquid discharged from the sampling nozzle 5 overflows from the upper portion of the washing pipe 14b to make it possible to wash the outer surface of the sampling nozzle 5. Although the method of washing the outer surface of the sampling nozzle 5 is different from the method of washing the outer surface of the sampling nozzle 4, this washing can be performed sufficiently by this method because the sampling nozzle 5 is smaller than the sampling nozzle 4 both in size and in surface area to be in contact with the liquid sample. Accordingly, the number of parts for obtaining functions equivalent to those of the electromagnetic valve 43 and tube 55 can be reduced. Of course, the same washing method as the washing method applied to the outer surface of the sampling nozzle 4 may be used for washing the outer surface of the sampling nozzle 5.

The residual sample in the staining vessel 12 is drawn off via the tubes 58 and 59 by the operation of the peristyle pump 19 when the electromagnetic valve 44 is opened.

The aforementioned operations are repeated for every sample. If these operations are stored in a computer in the form of programs for every sample and for every plural samples, the operations can be executed along the programs.

In this embodiment, the liquid sample is supplied to the staining vessel 12 by use of the sampling nozzle 4 moved by the lift 4A, and the stained liquid sample is moved to the flow cell unit 10 by use of the sampling nozzle 5 moved by the lift 5A, so that it is not necessary to provide a long flowing vessel for feeding the liquid sample. Accordingly, it is possible to prevent foreign matter from being mixed into the liquid sample or bubbles from being produced therein.

Because a filter 34 is provided in the inlet of the flow cell nozzle 32, foreign matter in the liquid sample which is larger than the size of a mesh of the filter 34 can be caught when the liquid sample is discharged. Furthermore, the sheath liquid is made to flow backwardly upon completion of the discharge of the liquid sample, the foreign matter caught by the filter 34 can be removed from the waste liquid nozzle 36 by the sheath liquid. Accordingly, foreign matter in the liquid sample can be removed efficiently and thoroughly without stopping testing wastefully to wash foreign matter or exchange the filter 34. Further, because the area of the filter can be reduced, the carry-over or dead volume from the preceding sample can be reduced.

Because the air vent port 31 is provided in the flow cell unit 10, bubbles produced in the flow cell unit 10 can be removed through the air vent port 31 by compressing the sheath liquid through the operations of the electromagnetic valves 46, 47 and 48 and the syringe pump 3. Because the air vent chamber 21 is provided in the tube 61 communicated with the washing liquid bottle 20, bubbles produced in the sheath liquid can be reserved in the air vent chamber 21, and the bubbles can be drawn off from the exhaust tube 63 by compression through the operations of the electromagnetic valves 46, 47 and 48 and the syringe pump 3.

Because the quantity of the liquid sample required for testing may be as small as the volume of the sampling nozzle 4 or 5, this embodiment can be applied to the test of blood or urine for infants or the like from which a large sampling quantity cannot be taken, and the quantity of the washing liquid for washing the sampling nozzles 4 and 5 may be also small.

Because the two sampling nozzles 4 and 5 are used, both the supply of -the liquid sample from the sample cup 11 to the staining vessel 12 and the discharge of the stained liquid sample to the flow cell unit 10 can be performed at the same time, so that the efficiency of testing is further improved.

According to the present invention, therefore it is possible to prevent foreign matter or bubbles in the liquid sample or the sheath liquid from entering the flow cell unit, so that there occurs no case where foreign matter or bubbles are image-picked up together with particles, and in a particle classification apparatus having an optical system for detecting particles, there is no fear that foreign matter or bubbles are judged as particles by mistake and a useless still frame image is thereby picked up. As a result, high-accurate testing can be performed without reducing the efficiency of the testing.

What is claimed is:

1. An intra-liquid particle classification apparatus using light scattering comprising a flow cell unit for enclosing a liquid sample by a sheath liquid to form a flow having a flat section, a sheath liquid supply means for supplying said sheath liquid to said flow cell unit, a sampling nozzle for sucking said liquid sample and for discharging said liquid sample into said flow cell unit, a moving mechanism for moving said sampling nozzle to said flow cell unit, a foreign matter catching means disposed at an inlet of said flow cell unit so as to catch foreign matter in said liquid sample, a foreign matter removing means for flowing back said sheath liquid from said flow cell unit so as to remove said foreign matter caught in said foreign matter catching means, a bubble removing means for removing bubbles in said flow cell unit and in said sheath liquid, said liquid sample in said flow cell unit being irradiated with light so that classification and counting of particles in said liquid sample are carried out on the basis of an image formed by the light scattered by said liquid sample, said flow cell unit including a flow cell for enclosing said liquid sample by said sheath liquid to form a flat flow, a flow cell nozzle having an upper portion brought in close contact with a forward end portion of said sampling nozzle so as to supply said flow cell with said liquid sample supplied from said sampling nozzle, sealing means for sealing a close contact portion between said sampling nozzle and said flow cell nozzle, and a sheath liquid inlet for supplying said flow cell with said sheath liquid supplied from said sheath supply means, said bubble removing means including an air vent port opened in an upper portion of said flow cell unit so as to compulsorily remove bubbles which are stored in an upper portion of said flow cell unit in response to supply of said sheath liquid with compression from said sheath supply means in a condition that said sampling nozzle is in close contact with said flow cell nozzle.

2. An intra-liquid particle classification apparatus using light scattering according to claim 1, in which said bubble removing means includes an air vent chamber communicated with said sheath liquid supply means so as to reserve bubbles produced in said sheath liquid, and an air outlet for exhausting bubbles reserved in said air vent chamber.

3. An intra-liquid particle classification apparatus using light scattering according to claim 1, in which said foreign matter catching means is a filter provided at an inlet of said flow cell nozzle.

4. An intra-liquid particle classification apparatus using light scattering according to claim 1, in which said foreign matter removing means includes an outlet provided on the upstream side of said foreign matter catching means.

* * * * *